United States Patent
Takeuchi et al.

(10) Patent No.: US 11,940,432 B2
(45) Date of Patent: *Mar. 26, 2024

(54) GAS DETECTOR

(71) Applicants: Figaro Engineering Inc., Minoo (JP); New Cosmos Electric Co., Ltd., Osaka (JP); University Public Corporation Osaka, Osaka (JP)

(72) Inventors: Masato Takeuchi, Sakai (JP); Junpei Furuno, Sakai (JP); Kenta Fukui, Sakai (JP); Kuniyuki Izawa, Minoo (JP); Masakazu Sai, Minoo (JP); Hirokazu Mitsuhashi, Osaka (JP); Takafumi Taniguchi, Osaka (JP)

(73) Assignees: FIGARO ENGINEERING INC., Osaka (JP); NEW COSMOS ELECTRIC CO., LTD., Osaka (JP); UNIVERSITY PUBLIC CORPORATION OSAKA, Osaka (JP)

( * ) Notice: Subject to any disclaimer, the term of this patent is extended or adjusted under 35 U.S.C. 154(b) by 559 days.

This patent is subject to a terminal disclaimer.

(21) Appl. No.: 17/267,059

(22) PCT Filed: Jul. 25, 2019

(86) PCT No.: PCT/JP2019/029238
§ 371 (c)(1),
(2) Date: Feb. 9, 2021

(87) PCT Pub. No.: WO2020/031723
PCT Pub. Date: Feb. 13, 2020

(65) Prior Publication Data
US 2021/0164951 A1 Jun. 3, 2021

(30) Foreign Application Priority Data
Aug. 10, 2018 (JP) .................. 2018-151404

(51) Int. Cl.
*G01N 33/00* (2006.01)
*B01D 71/08* (2006.01)
*B01D 71/22* (2006.01)

(52) U.S. Cl.
CPC ........ *G01N 33/0014* (2013.01); *B01D 71/08* (2013.01); *B01D 71/22* (2013.01)

(58) Field of Classification Search
USPC ...................................... 73/31.07
See application file for complete search history.

(56) References Cited

U.S. PATENT DOCUMENTS

| 8,652,229 B2 | 2/2014 | Ensor et al. |
| 2014/0260986 A1 | 9/2014 | Ishizuka et al. |

(Continued)

FOREIGN PATENT DOCUMENTS

| JP | 2008-128687 A | 6/2008 |
| JP | 2010-509056 A | 3/2010 |

(Continued)

OTHER PUBLICATIONS

Official Communication issued in International Patent Application No. PCT/JP2019/029238, dated Oct. 8, 2019.

*Primary Examiner* — Clayton E. LaBalle
*Assistant Examiner* — Warren K Fenwick
(74) *Attorney, Agent, or Firm* — Keating & Bennett, LLP

(57) ABSTRACT

A gas detector comprises a gas detection unit and a filter introducing surrounding atmosphere to the gas detection unit. The filter comprises a gas-permeable organic polymer membrane having an acidic group or a basic group.

8 Claims, 2 Drawing Sheets

(56) References Cited

U.S. PATENT DOCUMENTS

2018/0224416 A1    8/2018  Tsai et al.
2021/0164929 A1*  6/2021  Takeuchi ............. B01D 53/228

FOREIGN PATENT DOCUMENTS

| JP | 2011-212565 A | 10/2011 |
| JP | 2013-111507 A | 6/2013 |
| JP | 2013-242269 A | 12/2013 |
| WO | 2016/152645 A1 | 9/2016 |
| WO | 2017/138190 A1 | 8/2017 |

* cited by examiner

GAS DETECTOR

FIELD OF THE INVENTION

The present invention relates to gas detectors such as gas sensors and, in particular, to their filters.

BACKGROUND ART

Organic polymer gas-permeable membranes such as PTFE (poly-tetra-fluoro-ethylene) membranes have been used as filters of gas sensors (see Patent Document 1: JP2008-128687A). These organic polymer gas-permeable membranes permeate promptly small molecules such as hydrogen but permeate slowly large molecules, if permeate them. Therefore, the inventors have noticed that organic polymer gas-permeable membranes are hopeful candidates of filers against siloxanes.

Patent Document 2 (JP2011-212565A) discloses to use ion-exchange resins such as Nafion (a trademark of E. I. Dupont) as filters against siloxane gases. It is disclosed that ion-exchange resins absorb or adsorb efficiently siloxane gases. Further, it is disclosed that the ion-exchange resin may have bead-like forms and that the Nafion may be supported on silica supports. Patent Document 3 (WO2017-138190A) discloses mesoporous silicas including sulfo group can polymerize siloxane molecules in the mesoporous silica.

PRIOR DOCUMENT LIST

Patent Documents

Patent Document 1: JP2008-128687A
Patent Document 2: JP2011-212565A
Patent Document 3: WO2017-138190A

SUMMARY OF THE INVENTION

Problem to be Solved by the Invention

When organic polymer gas-permeable membranes are exposed to siloxane gases for a long while, the siloxane molecules are accumulated in the membranes and finally permeate the membranes such that they may poison the gas detection units.

The object of the invention is to fix siloxane molecules in organic polymer gas-permeable membranes and to prevent the permeation of siloxane molecules.

Means for Solving the Problem

A gas detector according to the invention comprises a gas detection unit; and a filter introducing surrounding atmosphere to the gas detection unit and is characterized in that the filter comprises a gas-permeable organic polymer membrane having an acidic group or a basic group. Preferably, the gas detector is a gas sensor, and the gas sensor further comprises a housing accommodating the gas detection unit. Here, the filter is attached on the housing. In addition, the filter may be provided outside the housing. For example, a gas sensor without the filter may be accommodated in the downstream end, or the like, of a suction pipe, and, at the upstream position of the pipe, for example, at the tip end of the pipe, the filter according to the invention may be provided. The filter functions the same with this configuration to one attached on the housing.

Preferably, the gas-permeable organic polymer membrane has carboxyl group as the acidic group or amino group as the basic group. Other functional groups such as sulfo group or phosphoric acid group are usable. Siloxane molecules diffused in the membrane are prevented from desorption by the mechanism that the —(O—Si—O)— portion in the siloxane molecules are fixed on the acidic group or the basic group. When the siloxane concentration in the membrane increases and when the polymerization of the siloxane molecules hydrolyzed at the —(O—Si—O)— portion proceeds, the adsorbed siloxane molecules are completely fixed in the membrane. As described above, the introduction of an acidic group or a basic group makes the permeation of siloxane molecules through the membrane difficult. In the following, the gas-permeable organic polymer membrane is sometimes called the membrane, the polymer membrane, the permeable membrane, or the like.

Preferably, the gas-permeable organic polymer membrane is a membrane of polysaccharide. The membranes of polysaccharide preferably comprise cellulose; chitosan; fucoidan; or other acidic polysaccharaide. Some of polysaccharide membranes include inherently an acidic group such as carboxyl group or a basic group such as amino group, and, in addition, an acidic group such as sulfo group or a basic group may be introduced in polysaccharide membranes. Further, the acidic group or the basic group may be introduced in gas selective permeable membranes comprising a synthetic polymer. For example, protonic conductive polymers such as Nafion, hydroxyl ion-conductive polymers, or the like, may be introduced. Since PTFE membranes have gas-permeability that do not badly affect the response of a gas sensor, as is indicated by Patent Document 1, and since cellulose membranes and the gas selective permeable membranes have high gas-permeability, the membrane does not substantially reduce the response of a gas sensor.

Particularly preferably, the gas-permeable organic polymer membrane is a carboxy-methyl-cellulose membrane having carboxyl group or a chitosan membrane having amino group.

The organic polymer membranes are formed by casting; spin-coating; roll-coating; and so on, and may be self-supported separate membranes or supported membranes on support membranes. The membranes are preferably fixed on the housings, and atmospheres outside the housings permeate the membranes and reach the gas detection units.

The mechanism of the gas-permeation of the membranes is arbitrary; for example, micro-pores are present in the membranes such that the micro-pores are continuous and have nm order pore diameters and gas molecules may diffuse in the micro-pores. Alternatively, the membranes have large free volumes (spaces not occupied by the polymer) such that gas molecules dissolved in the membranes may diffuse between the free volumes by hopping.

According to the invention, gases permeate through the membrane and reach the gas detection unit. The acidic group or basic group fixes the siloxane molecules in the membrane. Siloxane molecules in the membrane are prevented from free molecular motions and their postures are easily fixed. Therefore, they are stably fixed to the acidic groups or the basic groups and are easily reacted. On the contrary, according to patent document 2, the Nafion membrane is supported on the silica support, or the like, and gases do not permeate through the membrane. Further, the elimination mechanism of siloxane molecules is believed the polymerization of siloxane molecules adsorbed on the membrane surface by hydrolysis. In addition, the siloxane molecules are believed present on the interface between the Nafion membrane and

FEATURES FOR CARRYING OUT THE INVENTION

The best embodiment for carrying out the invention will be described.

Embodiment

Figure 3:
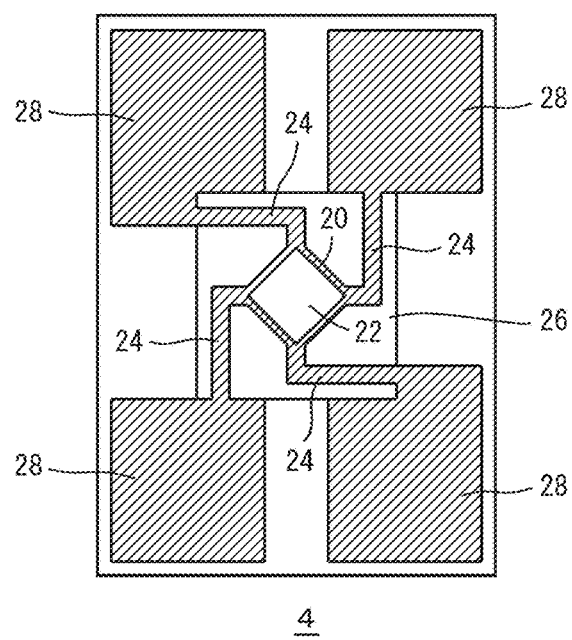
FIG. 3 is a plan view of a chip according to the embodiment.
Figure 4:
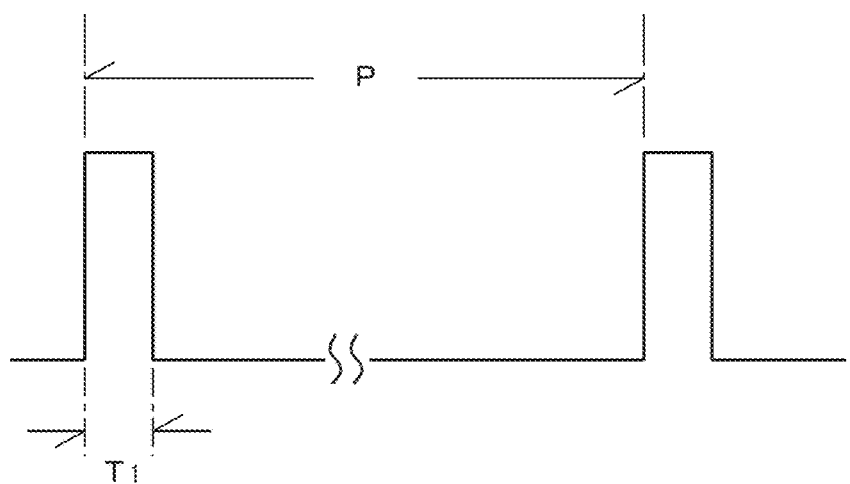
FIG. 4 indicates a driving pattern for the gas sensor according to the embodiment.
Figure 5:
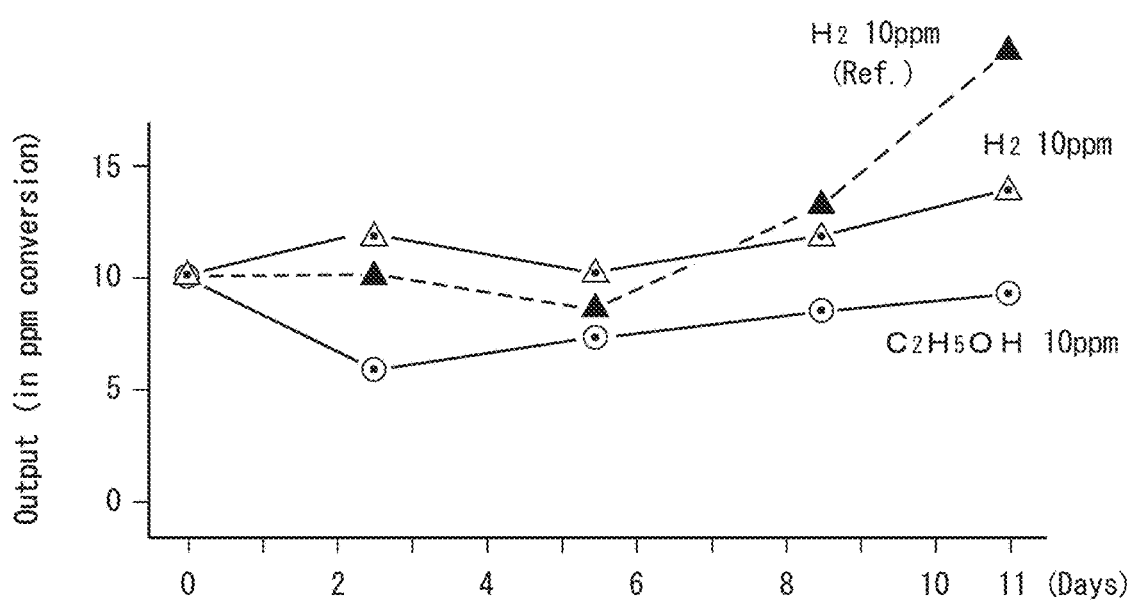
FIG. 5 is a characteristic view revealing the durability of the embodiment and that of a comparative example, against siloxane (D5×100 ppm).

FIGS. 1 to 4 indicate a gas sensor 2 according to the embodiment, and FIG. 5 indicates test results. The gas sensor 2 is, for example, provided with a Si chip 4, which is an example of a gas detection unit. The Si chip 4 is accommodated in a housing 5, such as a ceramic housing, and is fixed in the housing 5, for example, by die bonding. The opening of the housing 5 is covered by a ceramic lid 6 so that atmosphere outside the housing 5 is supplied through plural openings 7 to a filter 8. On the inside surface of the lid 6 (the surface towards the Si chip 4), the membranous filter 8 is attached. The species of the gas detection unit and the structure of the housing are arbitrary.

The filter 8 comprises, for example, a porous support membrane 10 and a gas-permeable organic membrane 12 overlayered on the support membrane. The gas-permeable organic membrane 12 will be sometimes simply called the membrane 12. The membrane 12 has a thickness of, for example, 0.1 micro-meter to 5 micro-meter. The support membrane 10 is a synthetic resin or a polysaccharide having continuous pores and has a thickness of, for example, 1 micro-meter to 100 micro-meter. In the embodiment, the support membrane 10 is provided to make the handling of the gas-permeable organic membrane 12 easy but it may not be provided.

The gas-permeable organic membrane 12 comprises, for example, a polysaccharide, such as carboxy-methyl-cellulose; cellulose-sulfate; fucoidan; and chitosan, and an acidic group, such as carboxyl group (carboxy-methyl-cellulose) and sulfo group (cellulose sulfate and fucoidan), or a basic group such as amino group (chitosan). Instead of these functional groups, phosphoric group or basic hydroxyl group may be included. In the following, acidic group and basic group will be simply called functional group.

Since long-chain molecules in polysaccharide membranes tend to be regularly ordered, continuous micro-pores are easily generated. And, these micro-pores are believed to be the gas diffusion path. In addition, the functional groups such as carboxyl or amino group have mutual hydrogen bond, and this hydrogen bond is speculated to cause the regular micro-pores. The functional groups are speculated to be present in the neighborhood of the micro-pores. The functional groups are believed to make hydrogen bond to the —(O—Si—O)— portion of the siloxane molecules and to decompose the siloxane molecules at this portion by hydrolysis such that the adsorbed siloxane molecules may be fixed in the membrane. Further, when the fixed siloxane molecules are accumulated in the membrane, the siloxane molecules polymerize mutually. As a ground, some of the inventors have confirmed that sulfo group in meso-porous silica polymerizes adsorbed siloxane molecules (Patent Document 3). It is speculated that a similar mechanism works in the membranes and siloxane molecules that have diffused into the membranes are polymerized by the mechanism Membranes such as carboxy-methyl-cellulose become water-soluble when treated with alkaline materials and become water-insoluble when treated with acidic materials. Therefore, the membranes can be formed from the water-soluble state and can be converted into the water-insoluble membranes by acid treatment. Membranes not suitable for the treatment between the water-soluble state and water-insoluble state can be formed with an adequate solvent and be converted into stable membranes by removing the solvent.

Other than the polysaccharide membrane, highly gas-permeable synthetic resin membranes, which have been used as gas selective permeable membranes, are suitable for the introduction of acidic or basic group. For example, Nafion may be introduced into gas selective permeable membranes such as fluoropolymers. Both the materials for gas selective permeable membranes (fluoropolymer synthetic resin membranes) and the material for Nafion membranes are commercially available as their solutions. When mixing them and forming the membrane, sulfo group may be introduced into the gas selective permeable membranes.

FIG. 3 indicates the Si chip 4; the Si chip 4 is provided with a micro-hotplate 20 with electrodes and a heater, on a cavity 26. The hotplate 20 is supported by beams 24 and has a metal oxide semiconductor 22 on it. Indicated by 28 are pads.

Figure 1:
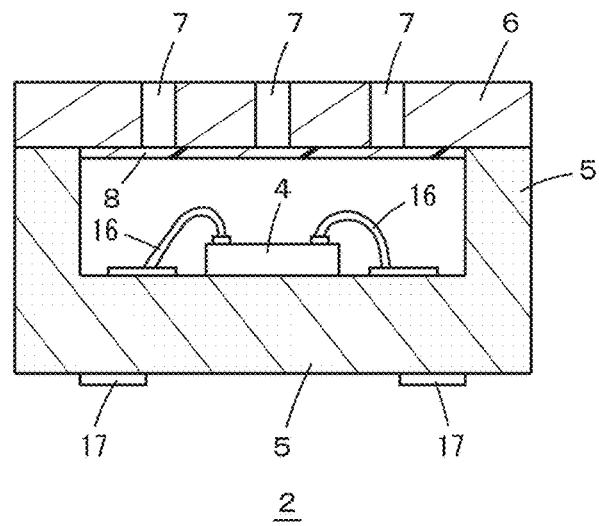
FIG. 1 is a cross-sectional view of a gas sensor according to the embodiment.
Figure 2:
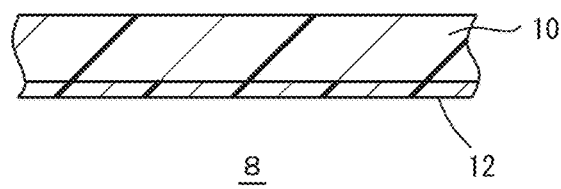
FIG. 2 is a cross-sectional view of a laminated membrane according to the embodiment.

As shown in FIG. 1, the pads of the Si chip 4 are connected to terminals 17 on the housing 5 via leads 16.

FIG. 4 indicates the operational pattern of the gas sensor 2. The gas sensor 2 is operated with a period P, is heated to an operational temperature of 250 degree Celsius to 450 degree Celsius for a period T1 for each period P, and gases are detected based upon the resistance of the metal oxide semiconductor when heated.

Other gas detection units than the Si chip 4 are usable, and other gas detection materials than metal oxide semiconductors are usable. For example, a contact combustion catalyst is usable as the gas detection material and, in that case, is supported on the hotplate 20 or by a heater coil not shown in the drawings. In addition, the metal oxide semiconductor 22 may be supported by other means than the hotplate 20. Further, electrochemical gas sensors that have a liquid or solid electrolyte and detection and counter electrodes connected to the electrolyte or further have a reference electrode connected to the electrolyte are usable as the gas detection unit. Siloxanes are poison to catalysts and make Pt catalyst, or the like, poisoned in the contact combustion gas sensors and Pt catalysts in the detection electrodes poisoned in the electrochemical gas sensors. The filters according to the invention prevents these gas sensors from being poisoned.

FIG. 5 shows the results of a durability test to siloxane (exposure for ten days in 100 ppm D5). In the embodiment (the solid lines), a thin membrane of carboxy-methyl-cellulose (thickness of about 0.5 micrometer) was used, and, in the comparative example (the broken line), a thin membrane of methyl-cellulose (thickness of about 0.4 micrometer) was used. The changes in the sensitivities for 10 ppm hydrogen and 10 ppm ethanol due to the D5 exposure were measured, and the sensitivities during the exposure and after the exposure are converted into hydrogen and ethanol concentrations by means of calibration lines before the exposure.

In the comparative example, hydrogen sensitivity increased from the latter half of the exposure, and this phenomenon indicates siloxane poisoning. In the embodiment, no siloxane poisoning was observed.

Experimental data on the carboxy-methyl-cellulose membrane are indicated. Other membranes comprising a gas-permeable organic polymer membrane with the introduction of an acidic or a basic group can fix siloxane molecules in the membrane and polymerize them such that the permeation of siloxane molecules may be prevented.

An acidic group or a basic group may be introduced into the organic polymer membranes by an arbitrary way. For example, sodium chloride, sugar, or fine oil particles are introduced into an emulsion of water and vinyl-acetate, and then a membrane is formed from them. Then, sodium chloride or sugar can be removed, or oil particles can be removed by oil such that a porous vinyl-acetate membrane is resultant. An aqueous solution of an organic sulfonic acid compound may be impregnated into the membrane and may be then dried, the resultant is a membrane having the organic sulfonic acid compound introduced in the micro-pores. Other porous organic polymer gas-permeable membranes than the vinyl-acetate membrane may be used for impregnating an aqueous solution of an organic acidic compound or an organic basic compound and then for drying.

The concentration of the organic acid compound or the organic basic compound in the organic membrane is arbitrary; for example, in the membranes having small pore diameters, the concentration becomes small. When the pore diameters become large, the concentrations may be increased. For example, when organic sulfonic acid compounds are supported in vinyl-acetate, the weight ratio between the organic sulfonic acid compounds and vinyl-acetate are preferably 1:100 to 30:100.

LIST OF SYMBOLS 2 gas sensor
4 Si chip (gas detection unit)
5 housing
6 lid
7 opening
8 filter
10 support membrane
12 gas-permeable organic membrane
16 lead
17 terminal
20 micro-hotplate
22 metal oxide semiconductor
24 beam
26 cavity
28 pad

The invention claimed is:

1. A gas detector comprising: a gas detection unit; and a filter introducing surrounding atmosphere to the gas detection unit,
wherein the filter comprises a gas-permeable organic polymer membrane having an acidic group or a basic group and wherein said gas-permeable organic polymer membrane is configured to make gases to be detected permeate said gas-permeable organic polymer membrane and to fix siloxane molecules in said gas-permeable organic polymer membrane.

2. The gas detector according to claim 1,
wherein the gas detector is a gas sensor, and
wherein the gas sensor further comprises a housing accommodating the gas detection unit and wherein the filter is attached on the housing.

3. The gas detector according to claim 2,
wherein said gas-permeable organic polymer membrane has carboxyl group as the acidic group or amino group as the basic group.

4. The gas detector according to claim 2,
wherein said gas-permeable organic polymer membrane is a membrane of polysaccharide.

5. The gas detector according to claim 2,
wherein said gas-permeable organic polymer membrane is a carboxy-methyl-cellulose membrane having carboxyl group or a chitosan membrane having amino group.

6. The gas detector according to claim 1,
wherein said gas-permeable organic polymer membrane has carboxyl group as the acidic group or amino group as the basic group.

7. The gas detector according to claim 1,
wherein said gas-permeable organic polymer membrane is a membrane of polysaccharide.

8. The gas detector according to claim 1,
wherein said gas-permeable organic polymer membrane is a carboxy-methyl-cellulose membrane having carboxyl group or a chitosan membrane having amino group.

* * * * *